United States Patent [19]

Davis et al.

[11] Patent Number: 4,500,291
[45] Date of Patent: Feb. 19, 1985

[54] METHOD OF FABRICATING DENTURES

[76] Inventors: Sammy G. Davis; Donna C. Gulling, both of 10319 E. 42nd St., Kansas City, Mo. 64133

[21] Appl. No.: 516,790

[22] Filed: Jul. 25, 1983

[51] Int. Cl.$^3$ .............................................. A61C 13/00
[52] U.S. Cl. .................................... 433/213; 433/213
[58] Field of Search .............. 433/167, 171, 191, 196, 433/199, 213; 264/16, 17, 18

[56] References Cited

U.S. PATENT DOCUMENTS

| 2,705,815 | 4/1955 | Brauer | 433/196 |
| 2,775,035 | 12/1956 | Beresin | 433/196 |
| 2,896,265 | 7/1959 | Chambers | 264/17 |
| 4,078,310 | 3/1978 | Horger, Jr. | 433/213 |
| 4,158,915 | 6/1979 | Stengel | 433/191 |
| 4,299,573 | 11/1981 | Ricci | 433/167 |
| 4,337,042 | 6/1982 | von Nostitz | 433/171 |
| 4,403,961 | 9/1983 | Gurney | 433/213 |

Primary Examiner—John J. Wilson
Attorney, Agent, or Firm—Richards, Harris & Medlock

[57] ABSTRACT

Impressions of the patient's upper and lower arches are prepared and a plaster of Paris model of each of the arches is cast. A wax plate is formed on each model around the palate and gingival areas surrounding the teeth. A tooth and the surrounding wax plate is removed exposing the plaster. A base, formed of fast cure acrylic material, is then formed on the exposed plaster. A replacement tooth is then placed in the base material.

6 Claims, 5 Drawing Figures

METHOD OF FABRICATING DENTURES

TECHNICAL FIELD

The invention pertains to removable denture restorations and more particularly to an economical method of fabricating dentures.

BACKGROUND ART

Conventional methods of manufacturing dentures involve many steps, are costly and time consuming. Normally, the dentist begins by taking an impression of the patient's upper and lower arches. A plaster model is prepared from the impression and an inverse impression of the plaster model is made. A wax plate, which contains indentations for teeth and gums, is then formed around the palate and gums of the original plaster model. This wax plate is removed from the model and artificial teeth are positioned in the indentations in the wax and the plate is placed on top of the inverse impression. The wax plate and impression are placed as a unit in the boiler and the wax is boiled off, leaving the artificial teeth in the inverse impression. Acrylic is then applied to the teeth while still in the inverse impression and the gum and other areas are built up with slow setting acrylics to form a denture plate. The inverse impression containing artificial teeth in acrylic is then placed in a cooker for at least six hours to harden. The plates are then removed from the inverse mold, buffed and ground to remove the excess acrylic and smooth the plate. Additional adjustments, such as further buildup of the acrylic, or grinding, are commonly required.

The foregoing process is extremely time consuming and so complex that it frequently requires several trips to the dentist to obtain dentures which fit. Accordingly, there is a need for a more accurate, efficient and economical method of preparing dentures which do not have the disadvantages of conventional prior art processes.

DISCLOSURE OF THE INVENTION

The present invention provides for an accurate, efficient and economical method of preparing denture plates. According to the preferred embodiment of the invention, impressions of the patient's upper and lower arches are prepared and a plaster of Paris model of each of the arches is cast. A wax plate is formed on each model around the palate and gingival areas surrounding the teeth. A tooth and the surrounding wax plate is removed exposing the plaster. A base, formed of fast cure acrylic material, is then formed on the exposed plaster. A replacement tooth is then placed in the base material.

BRIEF DESCRIPTION OF THE DRAWINGS

A more complete understanding of the present invention can be had by reference to the following Detailed Description in conjunction with the accompanying Drawings, wherein.

DETAILED DESCRIPTION

The present invention is aimed at providing an accurate, efficient and economical process for fabricating dentures.

Figure 1:
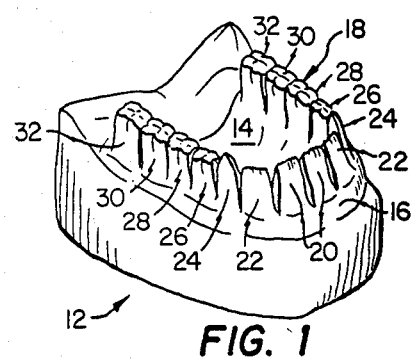
FIG. 1 is a perspective view of a plaster of Paris model of the patient's lower arch formed in one step of the present invention.

As conventional in most methods for making dentures, the dentist first makes an impression of the patient's upper and lower arches in alginate or other rubber base material. When the impression material is sufficiently set up, it is removed from the patient's mouth and allowed to completely harden. Referring to FIG. 1, a plaster model 10 of the patient's upper arch and a plaster model 12 of the patient's lower arch is prepared by pouring in conventional stone gypsum product, such as plaster of Paris, into the impression. When the plaster is set, the models 10 and 12 are then removed from the mold.

FIG. 1 illustrates a plaster model 12 of the patient's lower arch. The model reproduces the patient's palate 14, gingiva 16 and teeth 18. FIG. 1 illustrates a model in which all permanent teeth are present, although edentulous models will also be common. As best seen in FIG. 1, the model may contain a pair of central incisors 20, lateral incisors 22, cuspids 24, first and second bicuspids 26 and 28 and first and second molars 30 and 32.

Although FIG. 1 illustrates a model in which all of the patients teeth are present, such that the teeth of model 12 are plaster, the present invention can also be utilized where some of the patient's teeth have already been removed. Where the patient's teeth have already been removed, artificial plastic teeth may be inserted in wax in the model of FIG. 1. These artificial teeth are referred to in the art as a "set-up".

Figure 2:
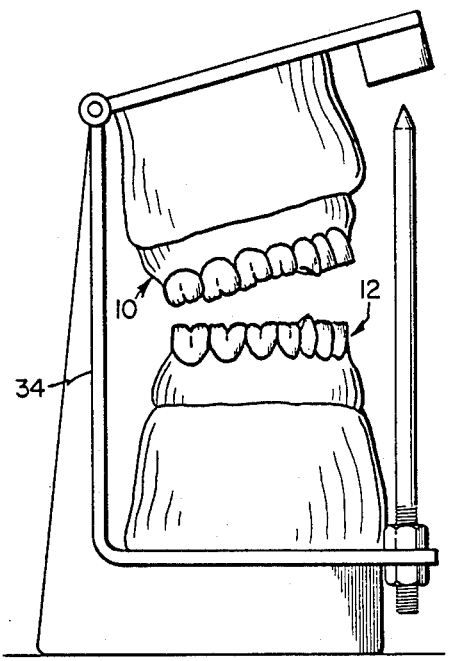
FIG. 2 is a side view of plaster of Paris models of the patient's upper and lower arches placed in a straight line articulator.

Referring now to FIG. 2, the plaster model 12 of the patient's lower arch and a model 10 of the patient's upper arch are placed in an articulator 34, such as a straight line articulator, to preserve the occlusal relationship in the patient's mouth. Once the proper adjustments have been made in the articulator 34, models 10 and 12 may be removed for processing.

Figure 3:
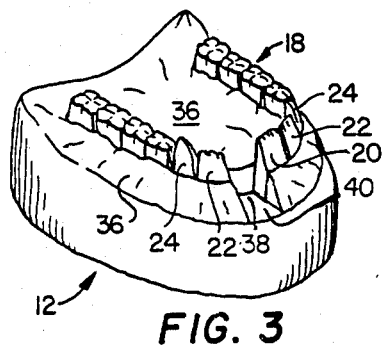
FIG. 3 is a perspective view of a plaster of Paris model of the patient's lower arch containing a wax plate in which one central incisor of the model have been removed.
Figure 4:
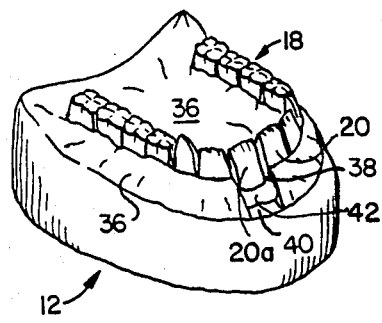
FIG. 4 is a perspective view of the model of FIG. 3 in which a replacement central incisor has been positioned on the model in an acrylic base built thereon.

FIGS. 3-4 illustrate the use of a model 12 of the patient's lower arch in the subsequent steps of the present invention. Although a model 12 of the patient's lower arch is shown for purposes of illustration, it will be understood that the steps of the process are identical with respect to the formation of dentures for the upper arch.

Referring now to FIG. 3, a wax plate 36 is formed over the palate 14 and around the gingiva 16 on the model 12. Strips of dental wax are heated until pliable and the wax is conformed by hand to the model by finger pressure. Thus formed, the wax plate 36 is then conformed to indentations and contours of the teeth and gingiva.

FIG. 3 also illustrates the removal of one of the central incisors 20 which is cut out of the plaster mold 12 to leave a gap 38 exposing plaster 40. The central incisor 20, if representing a patient's existing tooth, would be plaster and therefore would be removed by grinding, or the like. If the central incisor 20 were an artificial tooth, where the patient's tooth had been previously removed, the artificial tooth is plastic, and is therefore removed by cutting away wax 36 using a heated knife.

The exposed plaster 40 of gap 38 is then foiled with a nonstick material to facilitate the removal of the finished denture plate at a later time. Suitable nonstick material for this application might include, for example, common household products such as PAM or SCOTCHGUARD.

FIG. 4 illustrates the positioning of a replacement tooth 20a. A fast cure acrylic is applied to the exposed plaster 40 in gap 38 to form a base 42 for central incisor 20a. The acrylic base 42 may be formed, for example, by applying the small amount of polymer in powdered form and then "painting" this polymer with a liquid monomer. An exemplary fast cure acrylic suitable for such applications is the monomer and polymer combination sold by Lang Dental Manufacturing Company of Chicago, Ill. in their "Jet Kit".

Once the acrylic base 42 has been formed, the replacement central incisor 20a is placed in the base and allowed to set for 4 or 5 minutes until the acrylic is sufficiently hard to resist misalignment.

Figure 5:
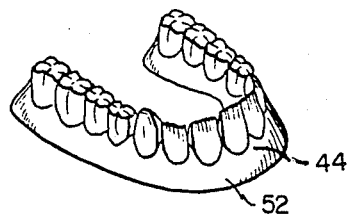
FIG. 5 illustrates a finished denture plate for the patient's lower arch.

The process continues by removing each plaster tooth or artificial tooth until all replacement teeth have been mounted to plaster 40 using the acrylic base 42. Each tooth is removed and replaced with a replacement tooth, one at a time, to ensure proper alignment. After central incisors 20 have been replaced, the lateral incisors 22; cuspids 24; bicuspids 26 and 28; and molars 30 and 32 are replaced, alternating from side to side and one at a time. Where the teeth in model 12 represent natural teeth of the patient, grinding of the plaster is required. Where the teeth in model 12 represent artificial teeth, cutting the wax to remove a plastic tooth is required. When the replacement process is complete, the wax 36 covering the gingiva is fully removed and additional fast cure acrylic is applied to form the front portion of the denture plate 44 (FIG. 5). Acrylic is applied to approximately the same thickness as the wax, or about 2 mm.

Referring now to FIG. 5, when the full denture plate 52 is complete, it is removed from the model 12 and ground to remove rough or overbuilt areas. Additional acrylic may be added where necessary to build up underdeveloped areas such that the thickness of acrylic will be approximately 2 millimeters except in areas subject to stress where the thickness may be up to 4 mm. Following the buildup and grinding steps, the plate 52 is then polished.

After buildup, grinding and polishing, the upper and lower denture plates are placed back on the models and the models are placed in the articulator to check the occlusion. A piece of carbon paper may be placed between the upper and lower plates to check the fit. If the fit is good, a trace of carbon will be formed on the surface; if improper, the replacement teeth can be ground down slightly until proper occlusion is obtained. The finished denture plate 52 is then lined with rebase material at the lab or the dentist office and inserted into the patient's mouth. After 5 to 10 minutes, the rebase material will set up and all excess rebase can be ground off by the dentist and the denture plates are ready for wear.

The method of the present invention is highly efficient, economical and more accurate than methods presently practiced. Conventional processes of denture fabrication typically require from 24 to 48 hours of laboratory preparation time. With the use of a fast cure acrylic, the elimination of cooking, and improved accuracy possible with the invention, laboratory preparation can be reduced with the present invention to 6 to 8 hours. Since the method of the present invention does not require the use of a boiler to remove wax or a cooker to harden the acrylic, the steps of boiling and cooking are eliminated. Moreover, substantial cost and efficiency advantages accrue from the ability to develop the denture by buildup or grinding of gingival areas without repeating the time consuming cooking process each time acrylic material is added to build up the gingival area.

The accuracy of the dentures prepared by the method of the present invention is enhanced by use of the plaster model to prepare the denture plates without using impressions of the models as in conventional prior art processes. This not only eliminates an unnecessary step in conventional processes with concomitant cost reduction of labor and materials cost, but more importantly, eliminates the most significant factor in denture inaccuracies.

Although a single embodiment of the invention has been illustrated in the accompanying Drawings and described in the foregoing Detailed Description, it will be understood that the invention is not limited to the embodiment disclosed, but is capable of numerous rearrangements, modifications and substitutions of parts and elements without departing from the spirit of the invention.

We claim:

1. A method for fabricating denture plates, comprising the steps of:
    preparing an impression of the patient's arch;
    casting a plaster model of the patient's arch;
    forming a wax plate to the contour of the palate and gingiva of the model;
    removing one of the teeth of the model to thereby expose the base of the model;
    preparing the denture plate by building up a base of acrylic material on the exposed base for the removed tooth and positioning a replacement tooth in the acrylic material to thereby replace the removed tooth; and
    building up the gingival area around the replacement tooth.

2. The method of claim 1 wherein the acrylic is a fast cure acrylic.

3. The method of claim 1 wherein the acrylic used to build up the gingiva area is a fast cure acrylic.

4. The method of claim 1 wherein the thickness of said wax plate is about 2 millimeters.

5. The method of claim 1 wherein the portion of the wax plate adjacent the gingival area on said model is removed prior to building up of the gingival area with said acrylic.

6. The method of claim 1 wherein the thickness of said acrylic of said finished denture plate is from about 2 to about 4 millimeters.

* * * * *